(12) United States Patent
Sokalski et al.

(10) Patent No.: US 10,094,798 B2
(45) Date of Patent: Oct. 9, 2018

(54) REFERENCE ELECTRODE AND AN ARRANGEMENT FOR AN ELECTROCHEMICAL MEASUREMENT

(71) Applicant: Abo Akademi University, Abo (FI)

(72) Inventors: Tomasz Sokalski, Turku (FI); Andrzej Lewenstam, Helsinki (FI); Zekra Mousavi, Turku (FI); Kim Granholm, Kaarina (FI)

(73) Assignee: Abo Akademi University, Abo (FI)

( * ) Notice: Subject to any disclaimer, the term of this patent is extended or adjusted under 35 U.S.C. 154(b) by 91 days.

(21) Appl. No.: 14/652,080

(22) PCT Filed: Dec. 12, 2013

(86) PCT No.: PCT/FI2013/051163
§ 371 (c)(1),
(2) Date: Jun. 12, 2015

(87) PCT Pub. No.: WO2014/091083
PCT Pub. Date: Jun. 19, 2014

(65) Prior Publication Data
US 2015/0323485 A1 Nov. 12, 2015

(30) Foreign Application Priority Data
Dec. 14, 2012 (FI) .................................... 20126315

(51) Int. Cl.
*G01N 27/26* (2006.01)
*G01N 27/30* (2006.01)
(Continued)

(52) U.S. Cl.
CPC ......... *G01N 27/301* (2013.01); *G01N 27/333* (2013.01); *G01N 27/4035* (2013.01)

(58) Field of Classification Search
CPC .... G01N 27/301; G01N 27/302; G01N 27/31; G01N 27/32
(Continued)

(56) References Cited

U.S. PATENT DOCUMENTS 4,589,418 A † 5/1986 Gopikanth
4,908,117 A † 3/1990 Kinlen
(Continued)

FOREIGN PATENT DOCUMENTS

| DE | 32 28 647 | 2/1984 |
|---|---|---|
| DE | 195 33 059 | 3/1997 |
| WO | WO 2012/074356 | 6/2012 |

OTHER PUBLICATIONS

DE19533059 English Translation.*
(Continued)

*Primary Examiner* — Bach T Dinh
(74) *Attorney, Agent, or Firm* — James C. Lydon (57) ABSTRACT

The present invention relates to the field of measuring and to electrochemical measurement, and more particularly to a reference electrode and to an arrangement for an electrochemical measurement. A reference electrode (13) for an electrochemical measurement according to the present invention comprises an inner reference element (14), which inner reference element (14) has been embedded into a solid electrochemically active composite material (15). An arrangement (16) for an electrochemical measurement comprises an inner reference element (17) and at least one indicator electrode (19), (20), which inner reference element (17) and the at least one indicator electrode (19), (20) have been embedded into a solid electrochemically active composite material (18). The solution according to the present invention may be utilized in any kind of electrochemical (Continued)

measurement in the fields of e.g. clinical analysis, environmental analysis and industrial analysis.

7 Claims, 8 Drawing Sheets

(51) Int. Cl.
    *G01N 27/333*     (2006.01)
    *G01N 27/403*     (2006.01)

(58) Field of Classification Search
    USPC .................................. 204/433, 435
    See application file for complete search history.

(56) References Cited

U.S. PATENT DOCUMENTS

| | | | |
|---|---|---|---|
| 4,927,518 A † | 5/1990 | Tauber | |
| 4,959,138 A * | 9/1990 | Brinkmann | G01N 27/30 |
| | | | 204/401 |
| 5,018,527 A | 5/1991 | Pfab et al. | 128/635 |
| 6,468,408 B2 | 10/2002 | Thrier et al. | 204/435 |
| 2001/0025790 A1* | 10/2001 | Thrier | G01N 27/401 |
| | | | 204/435 |
| 2003/0183517 A1 | 10/2003 | Ehrismann et al. | 204/296 |
| 2005/0147736 A1 | 7/2005 | Hsiung et al. | 427/58 |
| 2008/0053826 A1 | 3/2008 | Hsiung et al. | 204/418 |
| 2008/0149501 A1 | 6/2008 | Heule et al. | 205/788.5 |
| 2009/0283404 A1* | 11/2009 | Kakiuchi | G01N 27/401 |
| | | | 204/435 |
| 2011/0042225 A1 | 2/2011 | Adeloju | 205/170 |

OTHER PUBLICATIONS

Diamond, "Evaluation of a New Solid-State Reference Electrode Junction Material for Ion-Selective Electrodes," 6 *Electroanalysis* 962 (1994).

Vonau et al., "An All-Solid-State Reference Electrode," 144 *Sensors and Actuators B: Chemical* 368 (2010).

Guth et al., "Solid-State Reference Electrodes for Potentiometric Sensors," 13 *J, Solid State Electrochem* 27 (2009).

\* cited by examiner
† cited by third party

REFERENCE ELECTRODE AND AN ARRANGEMENT FOR AN ELECTROCHEMICAL MEASUREMENT

FIELD OF THE INVENTION

The present invention relates to the field of measuring and to electrochemical measurement, and more particularly to a reference electrode and to an arrangement for an electrochemical measurement.

BACKGROUND OF THE INVENTION

Within electrochemical measurements a potentiometric measurement is a commonly used measurement technique. Here, a potentiometric measurement is illustrated as a typical example of an electrochemical measurement. In a potentiometric measurement a potentiometric sensor, i.e. an indicator electrode, is used to determine certain chemical properties, e.g. the concentration of some components of the analyte gas or the analyte solution. A potentiometric sensor is a type of electrochemical sensor that measures the electrical potential in zero current conditions. The signal is measured as the potential difference (voltage) between the indicator electrode and the reference electrode. The potential of the indicator electrode depends on the measured chemical properties e.g. the concentration of the analyte in the gas or solution phase.

In a potentiometric measurement the chemical information, i.e. the activity of ions is translated into easily measurable electrical potential. In a typical potentiometric measurement the measured cell potential ($E_{meas}$) consists of the indicator electrode potential ($E_{ind}$), reference electrode potential ($E_{ref}$) and the liquid junction potential ($E_j$):

$$E_{meas}=E_{ind}+E_{ref}+E_j$$

In potentiometric measurement the role of the reference electrode is to maintain a constant potential independent of the sample composition. In a typical potentiometric measurement the indicator electrode gives a selective response corresponding to the concentration of the analyte to be measured according to:

$$E=\text{const}+S \ln a_i$$

$$E=\text{const}+S \ln [a_i+\Sigma K_{ij}^{pot}(a_j)^{z_i/z_j}+L],$$

where E is the measured potential, $a_i$ is the activity of the measured analyte, S is the slope of the linear part of the calibration curve, $K_{ij}$ is the selectivity coefficient and L is the detection limit. In a potentiometric measurement the reference electrode is an indispensable and crucial component both in potentiometry and open-circuit sensor technology as well as a reference point in amperometric measurements.

Potentiometric ion sensors including ion-selective electrodes (ISEs) are an important subgroup of electrochemical sensors. Ion-selective electrodes are characterized by small size, portability, low energy consumption, and low cost, which are attractive features concerning practical applications.

Figure 1:
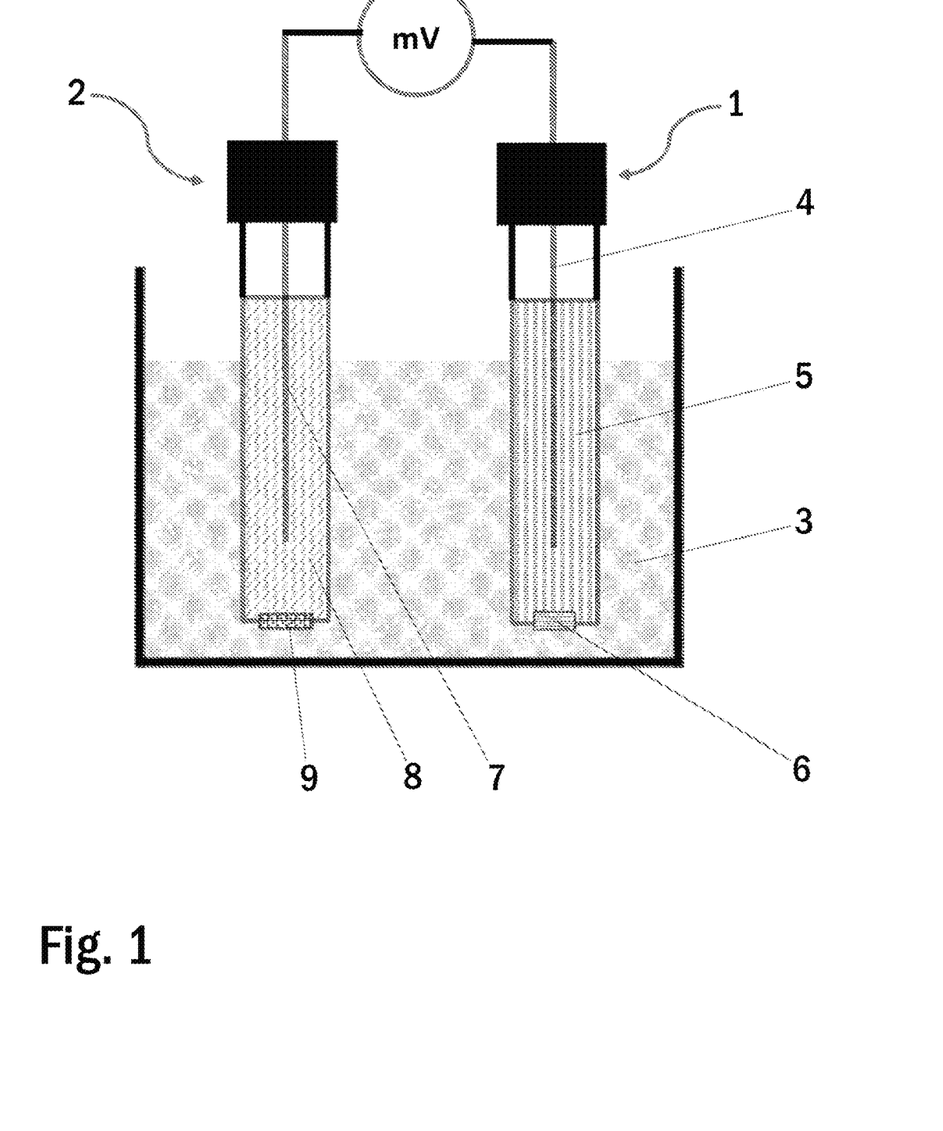
FIG. 1 shows one embodiment of an arrangement for an electrochemical measurement according to prior art.
Figure 2:
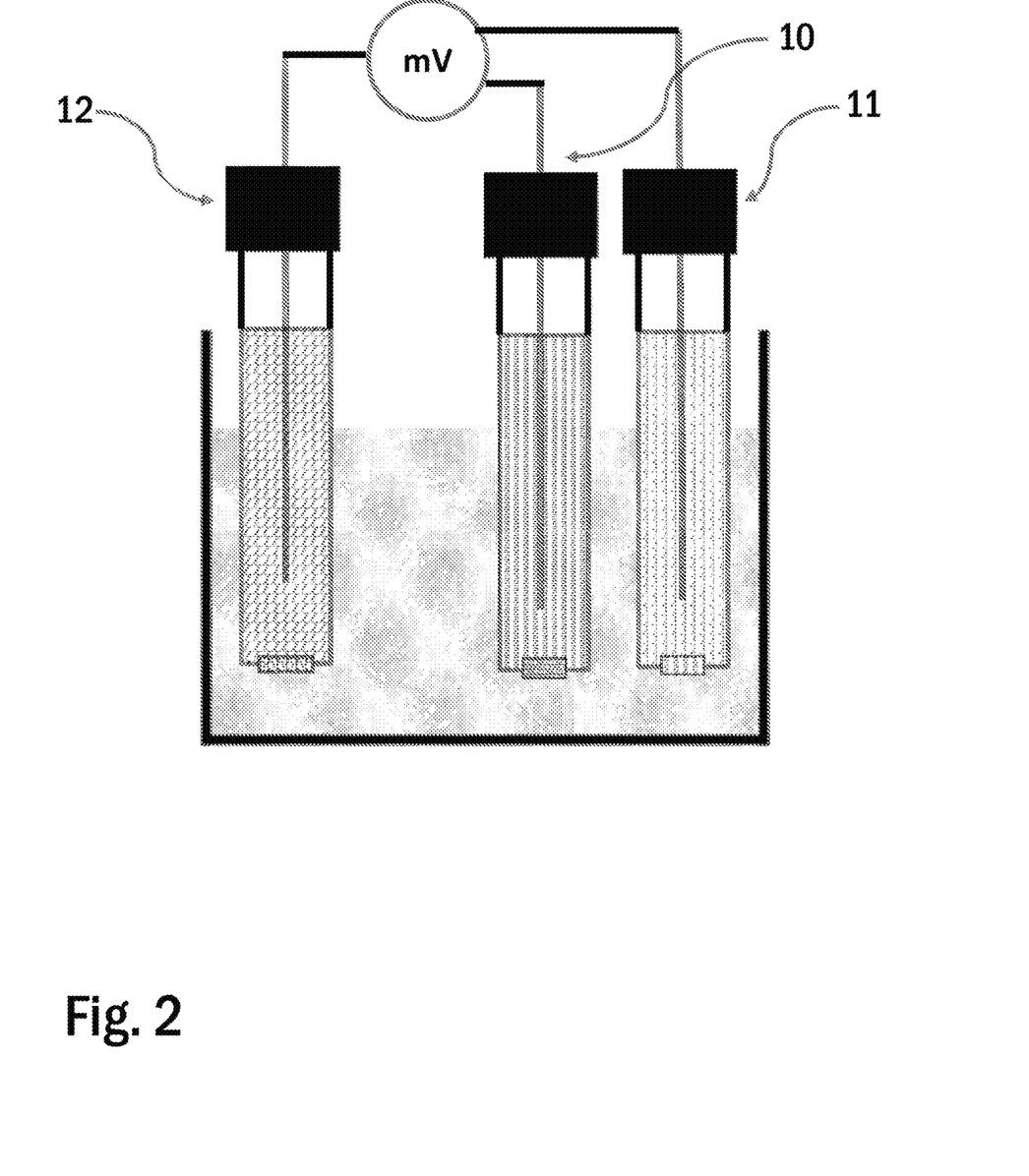
FIG. 2 shows another embodiment of an arrangement for an electrochemical measurement according to prior art.

In the following, the prior art will be described with reference to the accompanying drawings of FIGS. 1 to 2, of which:

FIG. 1 shows one embodiment of an arrangement for an electrochemical measurement according to prior art; and FIG. 2 shows another embodiment of an arrangement for an electrochemical measurement according to prior art.

FIG. 1 shows one embodiment of an arrangement for an electrochemical measurement according to the prior art. The arrangement for an electrochemical measurement according to the prior art comprises an ion-selective indicator electrode 1 and an external reference electrode 2. Both the ion-selective indicator electrode 1 and an external reference electrode 2 are placed in an analyte solution 3 the chemical properties of which solution 3 are to be measured. The potential difference between the electrodes 1 and 2 is measured. The potential produced is the sum of several individual potentials. Potential-determining processes always occur at the phase boundaries, e.g. between the solution 3 and the ion-selective membrane of the indicator electrode 1.

The ion-selective indicator electrode 1 of an arrangement for a electrochemical measurement according to the prior art comprises an internal reference element 4, an internal electrolyte solution 5 and an ion-selective membrane (ISM) 6. The external reference electrode 2 according to the prior art comprises a reference element 7 e.g. a reference electrode wire 7, a reference electrode solution 8 and a liquid junction 9.

As the potential in the arrangement for an electrochemical measurement according to the prior art is measured the external reference electrode 2 maintains a constant potential. Likewise, the ion-selective indicator electrode 1 gives a constant potential between the internal reference element 4 and the internal electrolyte solution 5 and also gives a constant potential between the internal electrolyte solution 5 and the ion-selective membrane 6. The ion-selective indicator electrode 1 according to the prior art is constructed so that if the ion to be measured is present in the analyte solution 3 then this ion can permeate the ion-selective membrane 6 of the ion-selective indicator electrode 1. This alters the electrochemical properties of the membrane and causes a change in potential.

Currently, ion-selective electrodes based on polymeric membranes containing neutral or charged carriers (ionophores) are available for the determination of a large number of inorganic and organic ions. Furthermore, during the past decade, the chemical sensing abilities of ISEs have been improved considerably. This can be attributed to several important findings, such as the considerable improvement in the lower detection limit of ISEs, new membrane materials, new sensing concepts, and deeper theoretical understanding and modeling of the electrochemical response of ion-selective electrodes.

FIG. 2 shows another embodiment of an arrangement for an electrochemical measurement according to the prior art. Another embodiment of an arrangement for an electrochemical measurement according to the prior art comprises two ion-selective indicator electrodes 10, 11 and an external reference electrode 12. One potential difference related to the first ion-selective indicator electrode is measured between the electrodes 10 and 12 and another potential difference related to the second ion-selective indicator electrode is measured between the electrodes 11 and 12.

The reference electrode 12 is an indispensable and crucial component in potentiometry and open-circuit sensor technology as well as a reference point in amperometric measurements. The failure of the reference electrode 12 means the failure of the entire system, so that none of the indicator electrode measurements can be collected. Thus, the quality of the reference electrode 12 is critical in electrochemical measurements, especially these where multi-parameter analyses are performed.

There have been alternative prior art electrochemical reference electrodes designed and studied in the past two decades. In one prior art electrochemical reference electrode design study there are equitransferent salts dispersed in a polymer or other solid. In one prior art embodiment polyvinyl resin doped with a very large amount of KCl has been used. Despite the heavy salt loading and large surface area in contact with the liquid sample, the reported leakage of KCl into the sample solution is less than what occurs with conventional ceramic frit junctions. The junction potential is quick to stabilize and relatively constant with time even in media with a very low ionic strength.

In another prior art electrochemical reference electrode design study there are other polymers or resins used, e.g. pressed $Al_2O_3$-PTFE, urea-formaldehyde, poly(methyl methacrylate)-propylene carbonate and/or polyester resin. Also in a third prior art electrochemical reference electrode design study an all solid reference electrode was introduced, consisting of a sintered Ag/AgCl mixture embedded in solid remelted KCl. Although these prior art concepts are rather different on the surface, the unifying factor is the controlled release of equitransferent salt from either a polymer material or a dense glass or ceramic sinter.

Unfortunately, all of the above-mentioned prior art electrochemical reference electrode design studies displayed relatively high electrical resistances (about 1-500 MΩ) for the reference electrode and it was reportedly not possible to get reproducible results.

Conventional prior art electrochemical reference electrodes have many problems and disadvantages. The prior art electrochemical reference electrodes are complicated and expensive to manufacture. The prior art electrochemical reference electrodes need to have the inner solution refilled and the liquid junction kept clog free and are therefore troublesome and maintenance intensive. The prior art electrochemical reference electrodes typically only work in upright position. Also the prior art electrochemical reference electrodes may easily foul or leak the internal solution into the sample. Also the prior art electrochemical reference electrodes are problematic as they have a separate physical body, are mechanically not very robust due to mainly glass construction, and are very difficult to miniaturize.

As mentioned above, there are a lot of deficiencies in the current reference electrodes. There is a clear demand in the market for a new type of electrochemical reference electrode that would be better and more efficient than the current prior art electrochemical reference electrode solutions. Likewise, there is a clear demand in the market for a new type of an arrangement for an electrochemical measurement that would be better and more efficient than the current prior art electrochemical measurement arrangement solutions.

BRIEF DESCRIPTION OF THE INVENTION

An object of the present invention is thus to provide a reference electrode and an arrangement for an electrochemical measurement so as to overcome the above problems and to alleviate the above disadvantages.

The objects of the invention are achieved by reference electrode for electrochemical measurement, which reference electrode comprises an inner reference element, which inner reference element has been embedded into a solid electrochemically active composite material.

Preferably, the inner reference element of the reference electrode is any kind of suitable reference element e.g. a silver wire covered with silver chloride.

Preferably, the solid electrochemically active composite material of a reference electrode is any kind of suitable solid and junctionless electrochemically active composite material e.g. a solid electrochemically active polymer composite material comprising inorganic salt such as potassium chloride dispersed in polymer matrix. Preferably, the reference electrode has been attached to a cable.

Preferably, the reference electrode is manufactured by chemical polymerization technique. Alternatively, the reference electrode is manufactured by injection moulding technique.

Furthermore, the objects of the invention are achieved by an arrangement for an electrochemical measurement, which arrangement comprises an inner reference element and at least one indicator electrode, which inner reference element and at least one indicator electrode have been embedded into a solid electrochemically active composite material.

Preferably, in the arrangement said at least one indicator electrode is an ion-selective indicator electrode. Preferably, in the arrangement the inner reference element is any kind of suitable reference element e.g. a silver wire covered with silver chloride. Preferably, in the arrangement the solid electrochemically active composite material is any kind of suitable solid and junctionless electrochemically active composite material e.g. a solid electrochemically active polymer composite material comprising inorganic salt such as potassium chloride dispersed in polymer matrix.

Preferably, in the arrangement the indicator electrodes each have an insulated electrically conducting element embedded into said solid electrochemically active composite material, and an ion-selective membrane arranged at the bare end of the said electrically conducting element. Preferably, the arrangement for an electrochemical measurement has been attached to a cable.

Preferably, the arrangement comprises multiple separate modularly arranged electrodes with one reference electrode and one or more indicator electrodes. Further preferably, the electrodes in the said electrochemical measurement arrangement are attachable to each other.

Preferably, the arrangement for an electrochemical measurement is manufactured by chemical polymerization technique. Alternatively, the arrangement for an electrochemical measurement is manufactured by injection moulding technique.

The prior art drawings of FIGS. 1 to 2 have been presented earlier. In the following, the invention will be described in greater detail by means of preferred embodiments with reference to the accompanying drawings of FIGS. 3 to 8.

DETAILED DESCRIPTION OF THE INVENTION

Figure 3:
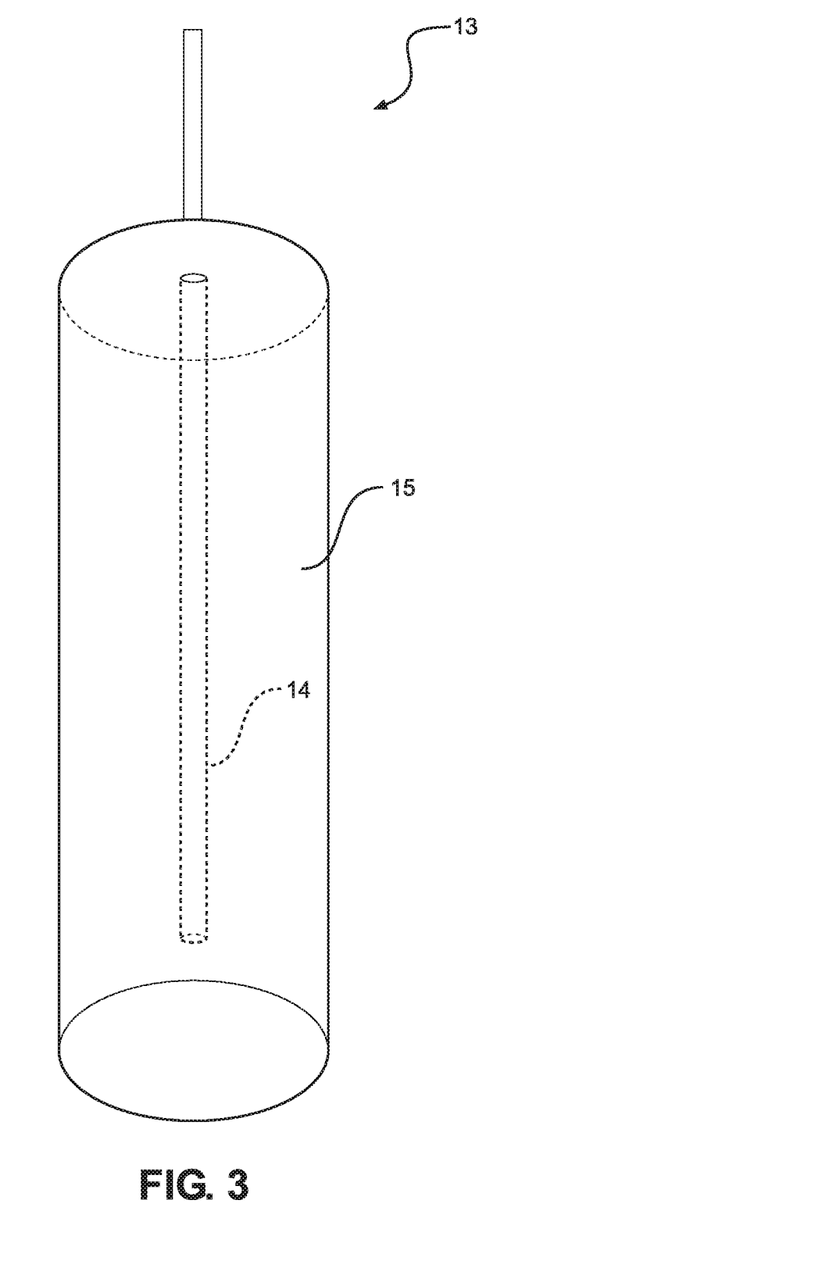
FIG. 3 shows one embodiment of a reference electrode according to the present invention.
Figure 4:
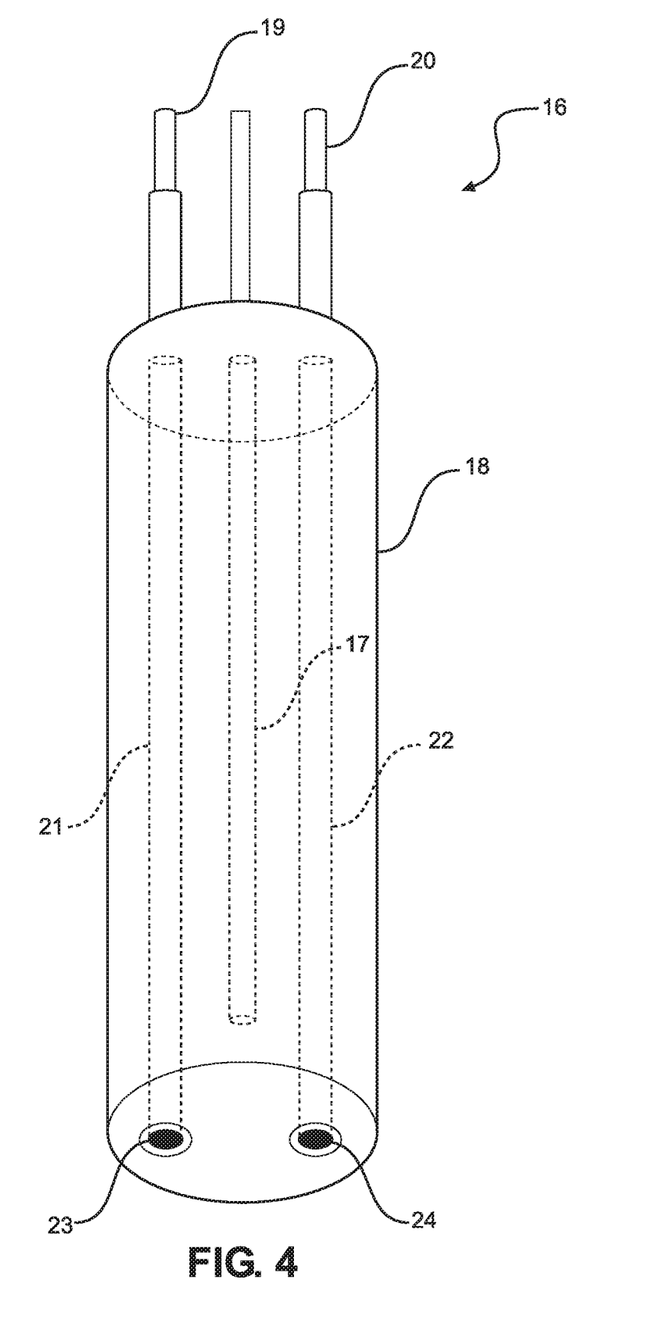
FIG. 4 shows one embodiment of an arrangement for an electrochemical measurement according to the present invention.

FIG. 3 shows one embodiment of a reference electrode according to the present invention. The reference electrode 13 according to the present invention comprises an inner reference element 14, which inner reference element 14 has been embedded into a solid electrochemically active composite material 15, e.g. a solid electrochemically active composite polymer material 15. The inner reference element 14 of a reference electrode 13 according to the present invention can be any kind of suitable reference element 14 e.g. a silver wire covered with silver chloride (Ag/AgCl). The solid electrochemically active composite material 15 of a reference electrode 13 according to the present invention can be any kind of suitable solid and junctionless electrochemically active composite material 15 e.g. a solid electrochemically active polymer material comprising inorganic salt such as potassium chloride (KCl) dispersed in polymer matrix FIG. 4 shows one embodiment of an arrangement for an electrochemical measurement according to the present invention. The arrangement 16 for an electrochemical measurement according to the present invention comprises an inner reference element 17, which inner reference element 17 has been embedded into a solid electrochemically active composite material 18, e.g. a solid electrochemically active composite polymer material 18. The arrangement 16 for an electrochemical measurement according to the present invention also comprises ion-selective indicator electrodes 19, 20, which ion-selective indicator electrodes 19, 20 have also been embedded into said solid electrochemically active composite material 18.

The solid electrochemically active composite material 18 of the arrangement 16 in conjunction with inner reference element 17, serves as the solid reference electrode and also as a casing for the indicator electrodes 19, 20.

The inner reference element 17 of an arrangement 16 for an electrochemical measurement according to the present invention can be any kind of suitable reference element 17 e.g. a silver wire covered with silver chloride (Ag/AgCl). The solid electrochemically active composite material 18 of an arrangement 16 for an electrochemical measurement according to the present invention can be any kind of suitable solid and junctionless electrochemically active composite material 18 e.g. a solid electrochemically active polymer material comprising inorganic salt such as potassium chloride (KCl) dispersed in polymer matrix. The ion-selective indicator electrodes 19, 20 of an arrangement 16 for an electrochemical measurement according to the present invention can each have an insulated electrically conducting element 21, 22 embedded into said solid electrochemically active composite material 18. The solid electrochemically active composite material 18 of the arrangement 16 in conjunction with inner reference element 17, serves as the solid reference electrode and also as a casing for the indicator electrodes 19, 20. The end part of the electrically conducting element 21, 22 of the ion-selective indicator electrodes 19, 20 does not have insulation. Instead an ion-selective membrane 23, 24 is arranged at the bare end of the said electrically conducting element 19, 20.

The reference electrode according to the present invention or the arrangement for an electrochemical measurement according to the present invention can be manufactured by chemical polymerization technique.

Figure 5:
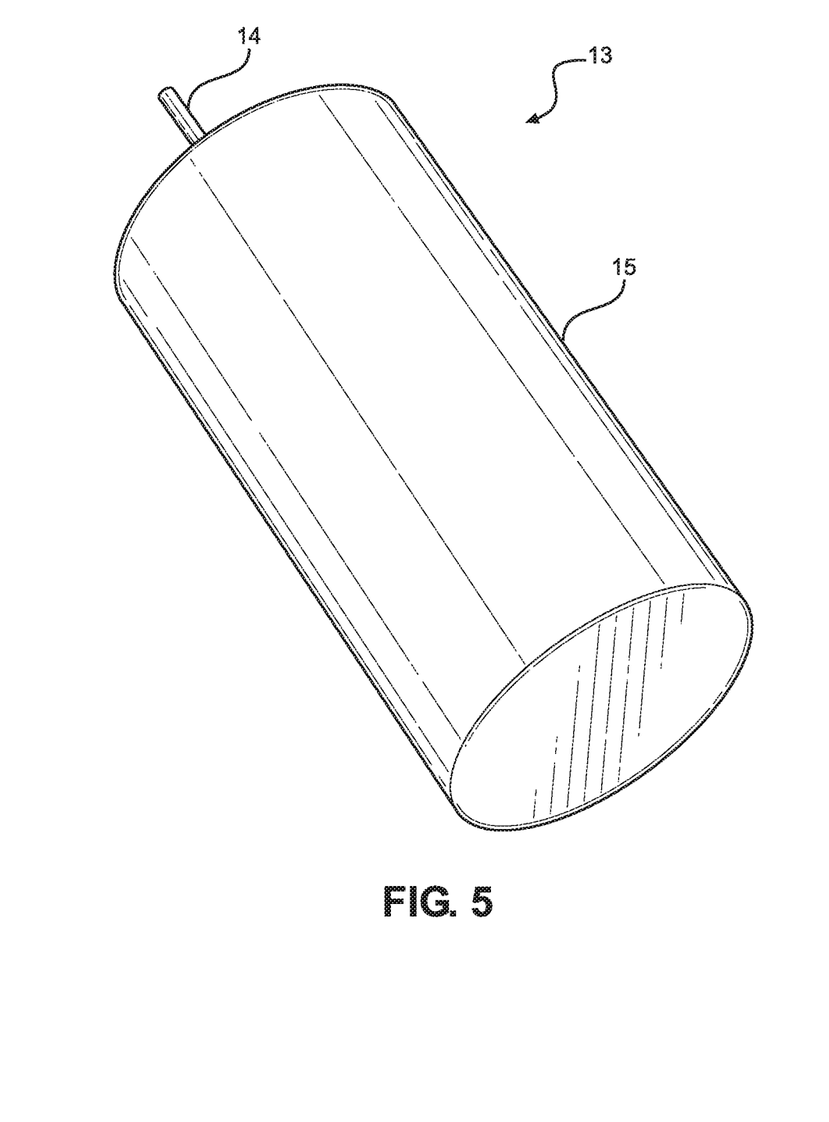
FIG. 5 shows one embodiment of a reference electrode according to the present invention manufactured by chemical polymerization technique.

FIG. 5 shows one embodiment of a reference electrode according to the present invention manufactured by chemical polymerization technique. The reference electrode 13 according to the present invention comprises an inner reference element 14, which inner reference element 14 has been embedded into a solid electrochemically active composite material 15, e.g. a solid electrochemically active composite polymer material 15. The electrochemically active composite material 15 of the arrangement in conjunction with inner reference element 14, serves as the solid reference electrode and also as a casing. The inner reference element 14 of a reference electrode 13 according to the present invention can be any kind of suitable reference element 14 e.g. a silver wire covered with silver chloride (Ag/AgCl). The solid electrochemically active composite material 15 of a reference electrode 13 according to the present invention can be any kind of suitable solid and junctionless electrochemically active composite material 15 e.g. a solid electrochemically active polymer material comprising inorganic salt such as potassium chloride (KCl) dispersed in polymer matrix.

In the chemical polymerization technique manufacturing process of one embodiment of a reference electrode according to the present invention first an inorganic salt such as potassium chloride (KCl) is mixed with e.g. polyvinyl acetate (PVAc) powder, vinyl acetate monomer and the photo initiator such as 2,2-dimethoxy-2-diphenylacetophenone. Thereafter, the polymerization is started by applying ultraviolet light and before the solid electrochemically active polymer material 15 is getting very hard the inner reference element 14 is inserted in the mixture and kept in the centre of the arrangement. The polymerization is continued by applying more ultraviolet light until the solid electrochemically active composite material 15 has become hard enough.

In the chemical polymerization technique manufacturing process of an arrangement for an electrochemical measurement according to the present invention first an inorganic salt such as potassium chloride (KCl) is mixed with e.g. polyvinyl acetate (PVAc) powder, vinyl acetate monomer and a photo initiator such as 2,2-dimethoxy-2-diphenylacetophenone. Thereafter, the polymerization is started by applying ultraviolet light and before the solid electrochemically active polymer material is getting very hard the inner reference element as well as the insulated electrically conducting element of the indicator electrode is inserted in the mixture. The insulated electrically conducting element of the indicator electrode may be e.g. a glassy carbon rod covered with Teflon, epoxy glue and a polyolefin shrink tube. The inner reference element is held in the centre of the arrangement and the insulated electrically conducting element of the indicator electrode is held at one side of the arrangement. The polymerization is continued by applying more ultraviolet light until the solid electrochemically active composite material has become hard enough. Thereafter the bottom part of the arrangement is removed and the uncovered side of the insulated, electrically conducting element of the indicator electrode is revealed.

The reference electrode according to the present invention or the arrangement for an electrochemical measurement according to the present invention can be manufactured by injection moulding technique.

Figure 6:
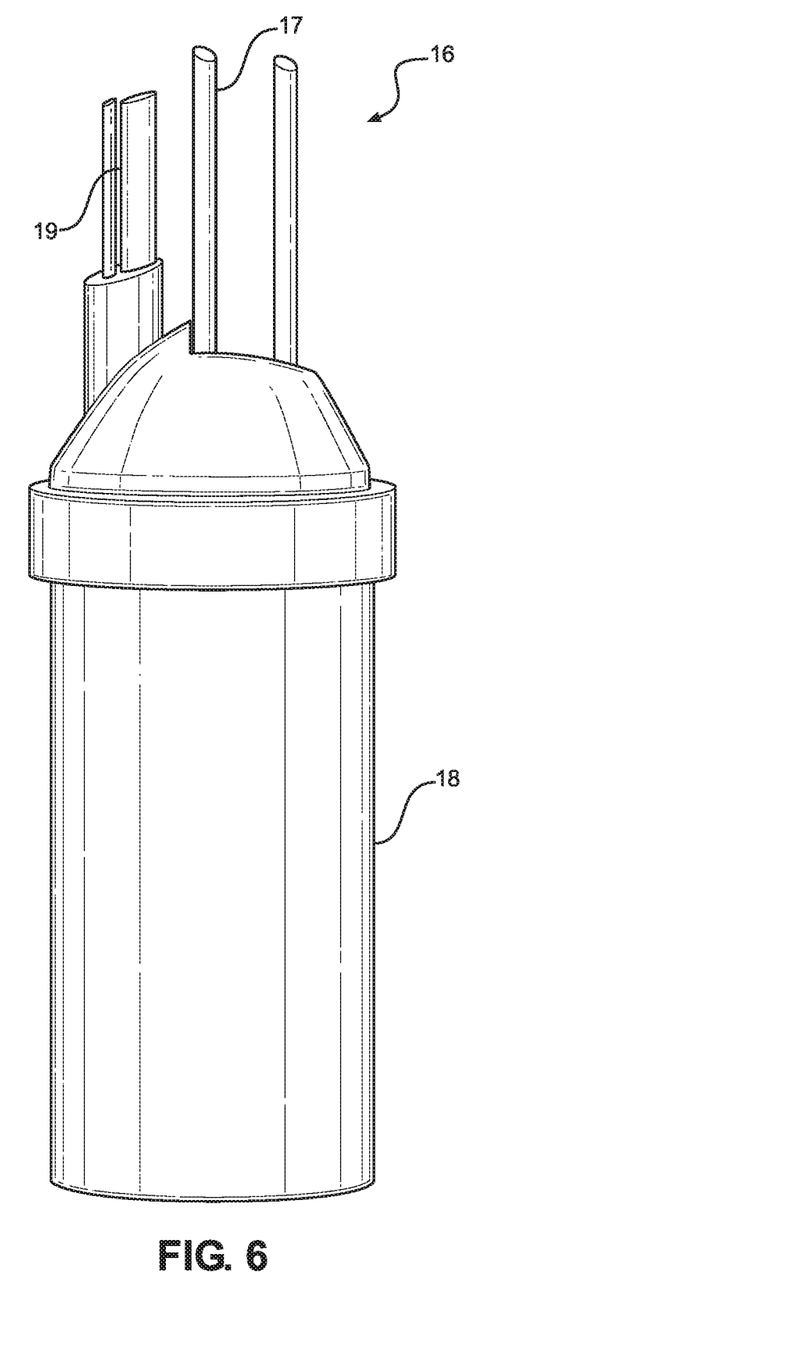
FIG. 6 shows one embodiment of an arrangement for an electrochemical measurement according to the present invention manufactured by injection moulding technique.

FIG. 6 shows one embodiment of an arrangement for an electrochemical measurement according to the present invention manufactured by injection moulding technique. The arrangement 16 for an electrochemical measurement according to the present invention comprises an inner reference element 17, which inner reference element 17 has been embedded into a solid electrochemically active composite material 18, e.g. a solid electrochemically active composite polymer material 18. The arrangement 16 for an electrochemical measurement according to the present invention also comprises an ion-selective indicator electrode 19, which electrode 19 has also been embedded into said solid electrochemically active composite material 18. The electrochemically active composite material 18 of the arrangement 16 in conjunction with inner reference element 17, serves as the solid reference electrode and also as a casing for the indicator electrode 19. The inner reference element 17 of an arrangement 16 for an electrochemical measurement according to the present invention can be any kind of suitable reference element 17 e.g. a silver wire covered with silver chloride (Ag/AgCl). The solid electrochemically active composite material 18 of an arrangement 16 for an electrochemical measurement according to the present invention can be any kind of suitable solid and junctionless electrochemically active composite material 18 e.g. a solid electrochemically active polymer material comprising inorganic salt such as potassium chloride (KCl) dispersed in matrix polymer. The ion-selective indicator electrode 19 of an arrangement 16 for an electrochemical measurement according to the present invention can have an insulated electrically conducting element embedded into said solid electrochemically active composite material 18. The end part of the electrically conducting element of the ion-selective indicator electrode 19 does not have insulation. Instead, an ion-selective membrane is arranged at the bare end of the said electrically conducting element 19.

In the injection moulding technique manufacturing process of one embodiment of an arrangement for an electrochemical measurement according to the present invention first an inorganic salt such as dry potassium chloride (KCl) is mixed with a polymer. Here the said polymer may be e.g. polyvinyl acetate (PVAc) powder. Thereafter, the inner reference element 17 is placed in the centre of an injection mould and the insulated electrically conducting element of the ion-selective indicator electrode 19 is placed at the side of the injection mould. Then the injection moulding is carried out. Thereafter, the bottom part of the arrangement is cut by using e.g. a saw with a diamond blade, and the uncovered side of the insulated, electrically conducting element of the indicator electrode 19 is revealed.

Figure 7:
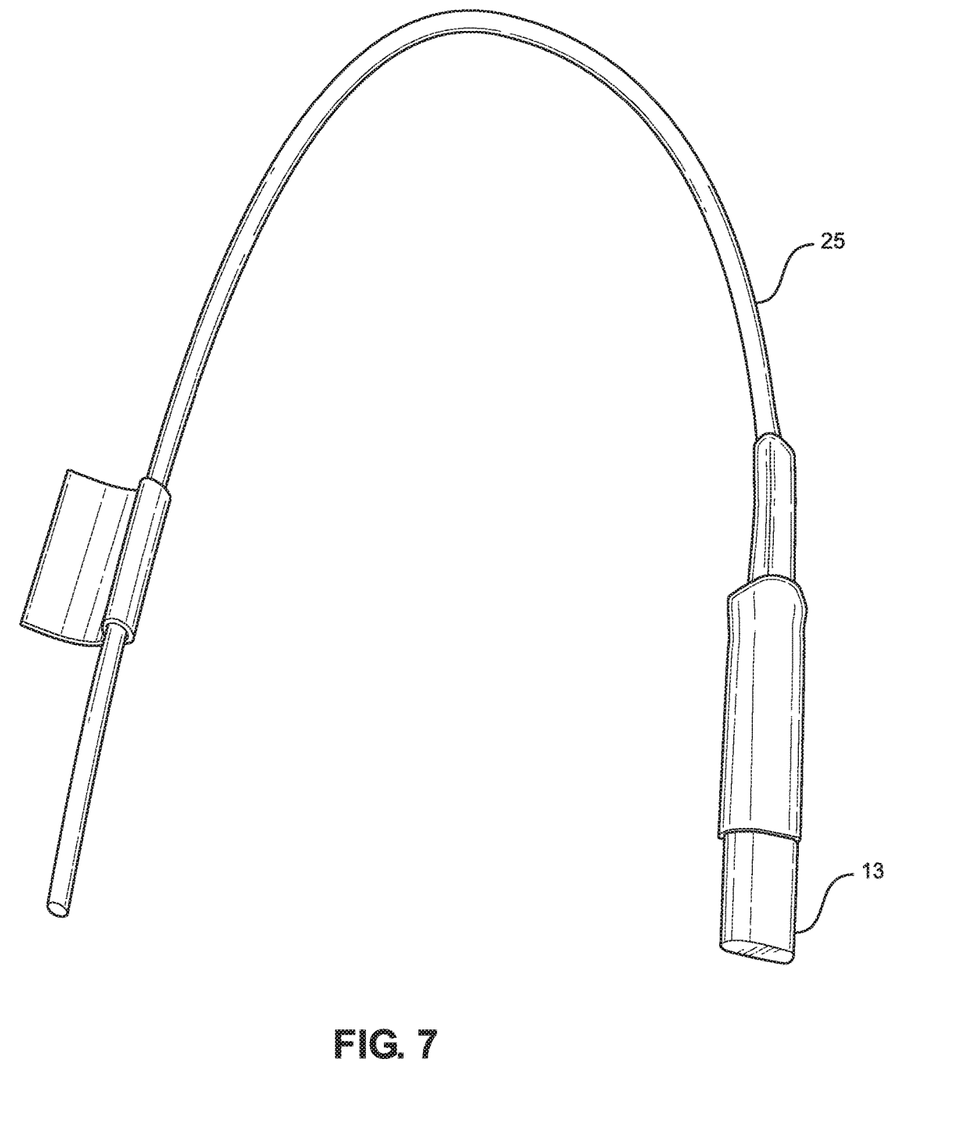
FIG. 7 shows one embodiment of a reference electrode with a cable according to the present invention obtained by injection moulding technique manufacturing process.

FIG. 7 shows one embodiment of a reference electrode with a cable according to the present invention obtained by injection moulding technique manufacturing process. The reference electrode with a cable according to the present invention comprises an electrochemical reference electrode 13, which reference electrode 13 has been attached to a cable 25. The fixings may be covered with epoxy glue and the body part may be filled e.g. with an electrically insulating silicon glue.

Figure 8:
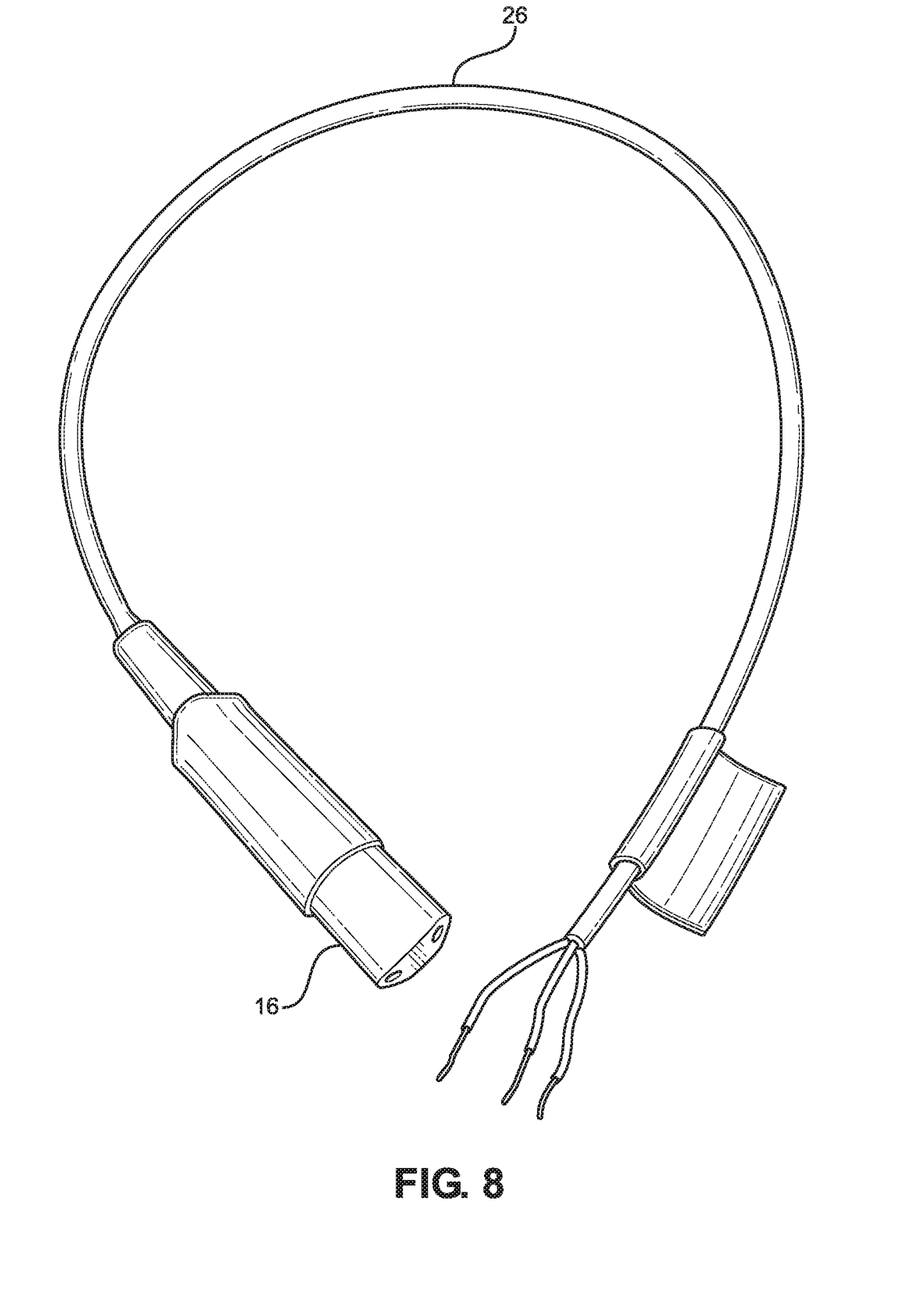
FIG. 8 shows one embodiment of an arrangement for an electrochemical measurement with a cable according to the present invention obtained by injection moulding technique manufacturing process.

FIG. 8 shows one embodiment of an arrangement for an electrochemical measurement with a cable according to the present invention obtained by injection moulding technique manufacturing process. The arrangement for an electrochemical measurement with a cable according to the present invention comprises an arrangement 16 for an electrochemical measurement, which arrangement 16 for an electrochemical measurement has been attached to a cable 26. The insulated electrically conducting element of the arrangement 16 for an electrochemical measurement may be fixed to the cable 26 by using a spring. The fixings may be covered with epoxy glue and the body part may be filled e.g. with an electrically insulating silicon glue.

The electrochemical measurement arrangement according to the present invention can comprise multiple, separate, modularly arranged electrodes with one reference electrode and one or more indicator electrodes. The electrodes in the said separate, modularly arranged electrochemical measurement arrangement may be attached to each other e.g. with clip connectors.

With the help of the electrochemical measurement arrangement according to the present invention one can achieve a solid state electrochemical platform that integrates the indicator electrodes and the reference electrode into a single body.

The electrochemical measurement arrangement according to the present invention produces substantial cost savings in manufacturing in comparison to electrochemical measurement arrangements according to prior art.

The electrochemical measurement arrangement according to the present invention is also very compact in size, volume and weight in comparison to electrochemical measurement arrangements according to prior art. Furthermore, the electrochemical measurement arrangement according to the present invention is easier to use and more reliable in use due to the considerably more robust structure. The electrochemical measurement arrangement according to the present invention acts at the same time as the physical body/encasing and the reference electrode.

The reference electrode and the electrochemical measurement arrangement according to the present invention may be utilized in any kind of electrochemical measurement in the fields of e.g. clinical analysis, environmental analysis and industrial analysis.

The electrochemical measurement arrangement according to the present invention is a robust and small size ion sensor arrangement, which retains the good analytical response of conventional electrodes. The reference electrode or the electrochemical measurement arrangement according to the present invention does not have an internal electrolyte solution, with additional benefits, one being the minimization of the contribution from the liquid junction. Additionally, the electrochemical measurement arrangement according to the present invention may be exposed to higher temperatures and pressures than liquid filled electrodes, and it does not need to be in an upright position. The electrochemical measurement arrangement according to the present invention does not need any refilling with internal solution and it can be manufactured in various shapes and sizes.

The electrochemical measurement arrangement according to the present invention is easy and cheap to manufacture, maintenance free, easy to miniaturize, works in any position, is mechanically robust and serves both as a physical body for indicator electrodes and the reference electrode. The electrochemical measurement arrangement according to the present invention also has limited fouling and limited leakage of the inorganic salt into the sample.

The electrochemical measurement arrangement according to the present invention has a simple structure and is therefore more reliable than prior art electrochemical measurement arrangement solutions. When implemented in the fields of clinical analysis, environmental analysis and industrial analysis the electrochemical measurement arrangement according to the present invention brings more savings, efficiency and reliability when compared to prior art solutions.

It will be obvious to a person skilled in the art that, as the technology advances, the inventive concept can be implemented in various ways. The invention and its embodiments are not limited to the examples described above but may vary within the scope of the claims.

The invention claimed is:

1. An arrangement for an electrochemical measurement, the arrangement (16) comprising
   a solid and junctionless electrochemically active composite material (18),
   a reference element (17), and
   at least one indicator electrode (19, 20),
   an external body consisting of said composite material (18) and, optionally, at least one ion-selective membrane,
      wherein the reference element (17) and at least one indicator electrode (19, 20) are embedded into said solid and junctionless electrochemically active composite material (18),
      wherein said composite material (18) comprises a solid electrochemically active polymer material comprising inorganic salt dispersed in polymer matrix, the solid and junctionless electrochemically active composite material (18) acting at the same time as an encasing for the reference element (17) and at least one indicator electrode (19, 20) and as a reference electrode in conjunction with the reference element (17),
      wherein said electrochemical measurement arrangement does not contain an internal electrolyte solution.

2. An arrangement according to claim 1, wherein said at least one indicator electrode (19, 20) is an ion-selective indicator electrode (19, 20).

3. An arrangement according to claim 1, wherein the reference element (17) is a silver wire covered with silver chloride.

4. An arrangement according to claim 1, wherein the indicator electrodes (19, 20) each have an insulated electrically conducting element (21, 22) embedded into said solid and junctionless electrochemically active composite material (18), and said ion-selective membrane (23, 24) is arranged at a bare end of the said electrically conducting element (21, 22).

5. An arrangement according to claim 1, wherein the arrangement (16) for an electrochemical measurement is attached to a cable (26).

6. An arrangement according to claim 1, wherein the arrangement (16) comprises multiple, separate, modularly arranged electrodes with one reference electrode (13) and one or more indicator electrodes (19, 20).

7. An arrangement according to claim 6, wherein the electrodes (13, 19, 20) in the said electrochemical measurement arrangement (16) are attachable to each other.

* * * * *